(12) United States Patent
Castellani

(10) Patent No.: US 12,178,841 B2
(45) Date of Patent: Dec. 31, 2024

(54) TREATMENT OF NON-CYSTIC FIBROSIS BRONCHIECTASIS

(71) Applicant: Zambon S.P.A., Bresso (IT)

(72) Inventor: Paola Castellani, Bresso (IT)

(73) Assignee: Zambon S.P.A., Bresso (Milan) (IT)

( * ) Notice: Subject to any disclaimer, the term of this patent is extended or adjusted under 35 U.S.C. 154(b) by 0 days.

(21) Appl. No.: 17/394,487

(22) Filed: Aug. 5, 2021

(65) Prior Publication Data
US 2023/0052317 A1 Feb. 16, 2023

(51) Int. Cl.
*A61K 38/12* (2006.01)
*A61K 9/00* (2006.01)
*A61P 31/04* (2006.01)

(52) U.S. Cl.
CPC ............ *A61K 38/12* (2013.01); *A61K 9/0078* (2013.01); *A61P 31/04* (2018.01)

(58) Field of Classification Search
CPC ........ A61K 38/12; A61K 9/0078; A61P 31/04
See application file for complete search history.

(56) References Cited

FOREIGN PATENT DOCUMENTS

WO WO-2016050933 A1 * 4/2016 ............. A61K 38/12

OTHER PUBLICATIONS

Steinfort et al., "Effect of long-term nebulized colistin on lung function and quality of life in patients with chronic bronchial sepsis," Internal Medicine Journal, 2007, 37: 495-498. (Year: 2007).*
Conly et al., "Colistin: The phoenix arises," Can. J. Infect. Dis. Med. Microbiol., 2006, 17(5): 267-269. (Year: 2006).*
Anonymous: "ISRCTN49790596: Inhaled proximin in the treatment of non-cystic fibrosis bronchiectasis", Sep. 9, 2014, url: https://www.isrctn.com/ISRCTN49790596.
Anonymous: "Long term efficacy and safety of inhaled colistimethate sodium in bronchiectasis subjects with chronic pseudomonas aeruginosa infection", ClinicalTrials.gov, Apr. 19, 2021, url: https://web.archive.org/web/20210419071926/https://clinicaltrials.gov/ct2/show/NCT03093974.
Anonymous: "Positive results from phase 3 promis-I study of CMS I-neb in patients with non-cystic fibrosis bronchiectasis presented at European Respiratory Society (ERS) Annual Meeting", Sep. 8, 2021 urs: https://www.zambon.com/sites/corporate/files/press/files/2021-09/zambon-press_release_final_8.09.21_eng.pdf.
International Search Report and Written Opinion of PCT/EP2022/071960 issue of Nov. 21, 2022.
Anonymous: "Promixin, 1 Million Internationale Einheiten (I.E.) Pulver Zur Herstellung einer Losung fur einen Vernebler" Sep. 1, 2019, pp. 1-4.
Blanco-Aparicio M. et al., "Eradication of Pseudomonas aeruginosa with inhaled colistin in adults with non-cystic fibrosis bronchiectasis", Chronic Respiratory Disease, vol. 16, Jan. 1, 2019, pp. 1-9.
Dhar R. et al., "Efficacy of nebulised colomycin in patients with non-cystic fibrosis bronchiectasis colonised with Pseudomonas aeruginosa", Thorax, vol. 65, No. 6, Jun. 1, 2010, p. 553.
European Search Report issued in corresponding EP application No. 21189819 on Jan. 21, 2022.
Haworth C. S. et al., "Inhaled colistin in patients with bronchiectasis and chronic Pseudomonas aeruginosa Infection", American Journal of Respiratory and Critical Care Medicine, vol. 189, No. 8, Apr. 15, 2014, pp. 975-982.
Lopez-Gil Otero Maria Del Mar et al, "Experience with nebulized colistin in patients with non-cystic fibrosis bronchiectasis colonized with Pseudomonas aeruginosa", Rev. Esp Quimioter, Jan. 1, 2019, pp. 217-223.
Clinical Trial of Zambon SpA "Long term efficacy and safety of inhaled colistimethate sodium in bronchiectasis subjects with chronic Pseudomonas Aeruginosa infection", Aug. 10, 2021.
European Medicines Agency completes review of polymyxin-based medicines, Dec. 16, 2014.
Grimwood K et al., "A new dawn: inhaled antibiotics for patients with bronchiectasis", The Lancet Respiratory Medicine, Jan. 15, 2019 pp. 1-2.
Nice Advice 2014, "Non-cystic fibrosis bronchiectasis: colistimethate sodium", Evidence summary, Jan. 6, 2014.
Polverino E. et al., "European Respiratory Society guidelines for the management of adult bronchiectasis", Eur Respir J 2017; 50:1700629.
News Provided by Zambon S.p.A., "Zambon presents results from the two phase 3 PROMIS studies of CMS I-neb in patients with non-cystic fibrosis bronchiectasis at world bronchiectasis conference 2023", Jul. 18, 2023.

* cited by examiner

*Primary Examiner* — Julie Ha
(74) *Attorney, Agent, or Firm* — Silvia Salvadori, P.C.; Silvia Salvadori

(57) ABSTRACT

Reducing the frequency of pulmonary exacerbations in patients suffering from Non-Cystic Fibrosis Bronchiectasis (NCFB) by administering colistin is described.

6 Claims, 2 Drawing Sheets

FIGURE 1

| Characteristic | | Nebuliser system | | |
|---|---|---|---|---|
| | | Respironics I-neb AAD with 0.3mL (grey) medication chamber | Pari eflow rapid | Pari LC Sprint with Pari Boy SX compressor |
| | | Promixin dose placed in nebuliser system | | |
| | | 1 million IU in 1mL | 1 million IU in 3mL | 1 million IU in 3mL |
| (a) | Droplet Size Distribution; Median Particle Size: $d_{50}$ (μm) | 4.34 | 4.56 | 4.37 |
| (b) | Total Drug Delivered from Nebuliser mouthpiece # (Million IU) | 0.333 | 0.277 | 0.385 |
| (c) | Fine Particle Fraction (% < 5μm) | 59.55 | 58.19 | 57

FIGURE 2

| Characteristic | | Nebuliser system | | |
|---|---|---|---|---|
| | | Respironics I-neb AAD with 0.5mL (lilac) medication chamber | Pari eflow rapid | Pari LC Sprint with Pari Boy SX compressor |
| | | Promixin dose placed in nebuliser system | | |
| | | 1 million IU in 1mL | 2 million IU in 4mL | 2 million IU in 4mL |
| (a) | Droplet Size Distribution; Median Particle Size: $d_{50}$ (μm) | 4.81 | 4.31 | 4.35 |
| (b) | Total Drug Delivered from Nebuliser mouthpiece # (Million IU) | 0.579 | 0.601 | 0.861 |
| (c) | Fine Particle Fraction (% < 5μm) | 53.01 | 63.11 | 57.73 |
| (d) | Fine Particle Dose Delivered from Nebuliser mouthpiece # (Million IU < 5 μm) | 0.307 | 0.379 | 0.497 |
| (e) | Delivery Time # | 8 minutes, 29 seconds | 6 minutes, 38 seconds | 11 minutes, 32 seconds |
| (f) | Drug Delivery Rate from Nebuliser mouthpiece # (Million IU/minute) | 0.036 | 0.057 | 0.043 |

Measured using a simulated inhalation: exhalation (I:E) ratio of 1:1, a tidal volume of 500mL and 15 breathes per minute.
• All Promixin reconstituted with a 50:50 mixture of WFI and 0.9% saline to the recommended volume for each nebuliser system.

• Pari Boy SX operated at 1.6 bar pressure, 5.1L/min flow rate.

• (d) is calculated from (b) / 100 x (c)

• (f) = (d) / (e)

TREATMENT OF NON-CYSTIC FIBROSIS BRONCHIECTASIS

FIELD OF THE INVENTION

The field of the present invention relates to the use of the known antibiotic colistin for the clinical treatment of bronchiectasis accompanied by bacterial infections.

STATE OF THE ART

Non-cystic fibrosis bronchiectasis (NCFB) is a severe chronic illness characterized by irreversible dilation of airways and thickening of bronchial walls, chronic inflammation, repeated infections, and progressive obstruction of the airways. In contrast to cystic fibrosis bronchiectasis (CFB), which is a well-defined genetic disorder, NCFB is a terminal pathologic condition from a number of causes.

Non-cystic fibrosis bronchiectasis (NCFB) is an important health issue that is increasingly common and related to a considerably high mortality. It has higher incidence in older patients and females. Furthermore, the incidence of NCFB during the last decades is increasing due to early diagnosis with the use of high-resolution computed tomography (HRCT).

The main causes of NCFB include infections, and non-infectious conditions such as immune deficiencies, mucociliary clearance defects, bronchial obstruction, chronic obstructive pulmonary disease (COPD), idiopathic inflammatory disorders, and autoimmune diseases. The most common cause in the literature is post-infectious, although no underlying cause is identified.

There is frequent, and often underestimated, coexistence of NCFB with COPD. Other co-morbidities are more frequent in NCFB patients as compared to CFB ones.

Inhaled antibiotics are effective for CFB patients with *P. aeruginosa* infection, but their efficacy in NCFB has not been demonstrated. In fact, a number of pathogens are involved in the colonization of patients with bronchiectasis. The main pathogens are Gram-negative bacteria including: *Haemophilus influenza*, *Moraxella catarrhalis*, and *Pseudomonas aeruginosa*. The latter is associated with increased morbidity and mortality. Gram-positive bacteria (*Streptococcus pneumoniae* and *Staphylococcus aureus*) are rare. In addition, in NCFB, *P. aeruginosa* strains are frequently more resistant than those in CFB.

At present, there are no approved inhaled antibiotic therapies for NCFB patients. Treatment with inhaled ciprofloxacin has been under investigation in the last few years, with contradictory results. Specifically, ORBIT-4 and RESPIRE-1 trials showed clinical benefit (prolongation of the time of the first exacerbation and reduced rate of exacerbations in the treatment group compared to the placebo group), whereas the ORBIT-3 and RESPIRE-2 failed to achieve their primary endpoints.

Also tobramycin has been proposed for treating NCFB. A review of most of the clinical trials for NCFB has been published in (ref A. Amorim, 2013).

Notwithstanding the several clinical evidences gained in these last years, a conclusive result is still lacking. Guidelines for the treatment of bronchiectasis have been published by the European Respiratory Society. Their recommendations (Polverino E, Goeminne P C, McDonnell M J, et al. European Respiratory Society guidelines for the management of adult bronchiectasis. Eur Respir J 2017; 50:1700629 disclose a complex analysis of the clinical symptoms associated with bronchiectasis. Treatments of bronchiectasis with nebulized colistin 1 MU delivered twice daily through the I-neb, is reviewed but is said not to be associated with a statistically significant improvement in time to first exacerbation compared to placebo.

A recent review summarizes the results of the latest clinical trial (Grimwood, K.; Chang, A. B., A new dawn: inhaled antibiotics for patients with bronchiectasis, The Lancet Respiratory Medicine, Jan. 15, 2019.

However, to date, no therapies have been shown to cure or reverse the progression of the disease, even though in 2010, the British Thoracic Society published guidelines for the management of patients with NCFB [16]. The guidance recommends treating patients with NCFB, who are infected with *P. aeruginosa*, with chronic inhaled anti-pseudomonal antibiotics, namely gentamicin, tobramycin or colistimethate sodium.

Colistin is a polymixin antibiotic produced by certain strains of *Bacillus polymixa*. It consists of a cationic cyclic heptapeptide with a tripeptide side chain acylated at the N-terminus by a fatty acid through an α-amide linkage (Reviews of Anti-Infective Agents CID 2005; 40: 1033-41).

Two different forms of colistin are available for clinical use: colistin sulfate which is administered orally for bowel decontamination and topically as a powder for the treatment of bacterial skin infections, and colistimethate sodium (CMS) (also called colistin methanesulfate, pentasodium colistimethanesulfate, and colistin sulfonyl methate) for parenteral (intravenous, intramuscular, aerosolized and intrathecal/intraventricular) therapy.

Colistimethate sodium (CMS) represents the sulfomethylated form of colistin. CMS is readily hydrolyzed to form sulfomethylated derivatives, as well as colistin sulfate, the active form of the drug. Thus, CMS is considered to be a pro-drug of colistin, whereby "colistin" it is typically intended a mix of polymyxin E1 and polymyxin E2. Chemical abstracts have assigned the number 1066-17-7 for colistin. According to the European Pharmacopoeia, colistin should comprise more than 77% of Polymyxin E1, E2, E3, E1i and E1-7MOA, but less than 10% of each of the minor components Polymyxin E3, E1-i and E1-MOA. In some occurrences the term "Polymyxin E" is also used interchangeably with "colistin".

Colistin has recently gained a crucial role for the treatment of various types of infections (e.g. pneumonia, bacteremia, urinary tract infections) caused by Gram-negative pathogens expressing a multidrug resistance phenotype (e.g. non-fermenting Gram-negative pathogens, and carbapenem-resistant enterobacteria).

Colistimethate sodium is active against gram negative bacteria including *Pseudomonas aeruginosa, Acinetobacter baumannii* and *Klebsiella pneumoniae*.

Inhaled colistimethate sodium is licensed for managing pulmonary infections caused by *P. aeruginosa* in people with cystic fibrosis (CF). The authorization was granted based on a bibliographic submission. Acute pulmonary exacerbations occur frequently in CF and are associated with progressive morbidity and mortality. Approximately 25% of CF patients will not regain their lung function after a pulmonary exacerbation, pointing to the necessity for the optimal and aggressive treatment of these events.

The following colistimethate preparations are available:
  Colobreathe® dry powder for inhalation using the Turbospin inhaler. Each capsule contains 1.6625 million international units, equivalent to 125 mg of colistimethate sodium. This preparation is licensed only for chronic pulmonary infections in people aged 6 years and older.

Colomycin® injection powder for solution for inhalation using a nebuliser. Each vial contains 1 or 2 million international units of colistimethate sodium (dose equivalent not specified).

Promixin® powder for nebuliser solution. Each vial contains 1 million international units, equivalent to 80 mg colistimethate sodium.

However, there are currently no licensed colistimethate products for the treatment of non-cystic fibrosis bronchiectasis (NICE Advice 2014, "Non-cystic fibrosis bronchiectasis: colistimethate sodium", Evidence summary, 6 Jan. 2014). Furthermore, according to the summaries of product characteristics, colistimethate sodium is very commonly associated with adverse respiratory effects (affecting at least 1 in 10 people), including cough, dyspnoea, bronchospasm and sore throat. The summary of product characteristics for Promixin® states that there have been reports of *P. aeruginosa* acquiring resistance to colistimethate sodium during clinical use.

A phase II clinical trial published in 2014 (ref. Haworth, C. et al. Am. J. Respir. Crit. Care Med., 2014, 189(8), 975-982) disclosed the use of nebulized colistimethate in NCFB (PPCTP/001).

The PPCTP/001 trial enrolled bronchiectasis patients with two or more positive respiratory tract cultures for *P. aeruginosa* in the preceding 12 months and who were within three weeks of completing a course of antipseudomonal antibiotics for the treatment of an exacerbation. *P. aeruginosa* also had to be cultured from a sputum sample taken at the screening visit. Participants were randomised to receive colistimethate sodium (1 MIU [33 mg CBA]; n=73) or placebo (0.45% saline; n=71) via the I-neb nebulizer twice a day, for up to 6 months. The primary endpoint was time to exacerbation. Secondary endpoints included time to exacerbation based on adherence recorded by the I-neb, *P. aeruginosa* bacterial density, quality of life, and safety parameters.

In this trial, however, the median time to first exacerbation after treatment was not statistically different from the placebo group.

A desirable treatment for NCFB would require not only alleviating the clinical symptoms of bronchiectasis such as the frequency of pulmonary exacerbations and their severity, but also minimizing adverse side effects and reducing the systemic toxicity.

SUMMARY OF THE INVENTION

The present invention relates to colistimethate sodium (CMS), administered at a dose of at least 20 mg Colistin Base Activity (CBA) per day, to reduce the frequency of pulmonary exacerbations in patients suffering from Non-Cystic Fibrosis Bronchiectasis (NCFB) with *P. aeruginosa* infections. The amount of CMS is comprised of from 20 mg to 60 mg CBA per day, even more preferably 10-30 mg CBA twice a day.

A further object of the present invention is a composition for inhalation, nebulization or aerosol spray comprising Colistimethate sodium (CMS) in an amount of from at least 30-35 mg CBA/mL to 60-70 mg CBA/mL of sterile aqueous solution suitable for inhalation, for use in reducing the frequency of pulmonary exacerbations in patients suffering from Non-Cystic Fibrosis Bronchiectasis (NCFB) and *P. aeruginosa* infections.

A further embodiment of the present invention relates to a kit for use in reducing the frequency of pulmonary exacerbations in patients suffering from Non-Cystic Fibrosis Bronchiectasis (NCFB) and *P. aeruginosa* infection comprising:

at least one single dose vial with an amount of Colistimethate sodium (CMS) in powder comprised of from 30-35 mg CBA to 60-70 mg CBA, an aqueous sterile saline solution and a leaflet with instruction for the treatment of NCFB.

The kit is preferably further provided with a suitable nebulizer system.

The invention also relates to a method of reducing the frequency of pulmonary exacerbations in patients suffering from Non-Cystic Fibrosis Bronchiectasis (NCFB) and *P. aeruginosa* infections, said method comprising:

administering by inhalation to said patients a dose of at least 20 mg CBA colistimethate sodium (CMS) a day; and reducing said frequency of said pulmonary exacerbations in said patients.

BRIEF DESCRIPTION OF THE DRAWINGS

The present invention will be better understood with the accompanying drawings, wherein:

FIG. 1. Schematic of the features characterizing devices suitable for CMS inhalation.

FIG. 2. Schematic of the features characterizing devices suitable for CMS inhalation.

DETAILED DESCRIPTION OF THE INVENTION

Definitions

The term "colistin" as used herein comprises colistin sulfate (typically administered orally for bowel decontamination and topically as a powder for the treatment of bacterial skin infections) and colistimethate sodium (CMS).

As used herein, the term colistimethate sodium comprises: colistin methanesulfate, pentasodium colistimethanesulfate, and colistin sulfonyl methate. CMS represents the sulfomethylated form of colistin. In order to become an effective antimicrobial agent, the sulfomethyl groups of CMS need to be hydrolysed thereby liberating free amino-groups to colistin sulfate, the active form of the drug. Thus, CMS is considered to be a pro-drug of colistin.

The active ingredient of "colistin" is represented chemically by a mix of polymyxin E1 and polymyxin E2. Chemical abstracts have assigned the number 1066-17-7 for colistin. According to the European Pharmacopoeia, colistin should comprise more than 77% of Polymyxin E1, E2, E3, E1i and E1-7MOA, but less than 10% of each of the minor components Polymyxin E3, E1-i and E1-MOA.

According to the EMA (European Medicines Agency) doses of this antibiotic should always be expressed in IU (International Unit) of colistimethate sodium. However, where a different dosage indication is used, the following conversion table (Table 1) should be used (ref. "European Medicines Agency completes review of polymyxin-based medicines", Dec. 16, 2014):

TABLE 1 conversion table for colistin amounts and dosage (EMA)

| Colistimethate sodium (IU) | Colistimethate sodium mass (mg) | Colistin-base activity (CBA) (mg)[1] |
|---|---|---|
| 12 500 | 1 | 0.4 |
| 150 000 | 12 | 5 |
| 1 000 000 | 80 | 34 |
| 4 500 000 | 360 | 150 |
| 9 000 000 | 720 | 300 |

[1]Nominal potency of the drug substance = 12.500 IU/mg

CMS is authorized for parenteral (intravenous, intramuscular, inhalation, aerosolized and intrathecal/intraventricular) use, in the management of adult and paediatric chronic pulmonary infections due to *Pseudomonas*.

CMS can be found under the following commercial names:

Colobreathe® dry powder for inhalation. Each capsule contains 1.6625 million international units, equivalent to 125 mg of colistimethate sodium. This preparation is licensed only for chronic pulmonary infections in people aged 6 years and older.

Colomycin® injection powder for solution for inhalation using a nebuliser. Each vial contains 1 or 2 million international units of colistimethate sodium (dose equivalent not specified).

Promixin®/Tadim®: powder (1 million international units).

As used herein, the term "about" is intended to refer to a range when a point value is given, the range comprising at least a 2%+/− of the given value.

As used herein the term "pulmonary exacerbation" in a patient refers to the presence concurrently of at least 3 of the following 8 symptoms/signs for at least 24 hours:
increased cough;
increased sputum volume and/or consistency;
increased sputum purulence;
new or increased haemoptysis;
increased wheezing;
increased dyspnoea;
increased fatigue/malaise;
episodes of fever (temperature≥38° C.)
and it is clinically determined that the subject requires and is prescribed systemic antibiotic therapy. A new pulmonary exacerbation is only considered to occur if there are at least 14 days between the end of the course of systemic antibiotics and the onset of new qualifying symptoms. (Note: A pulmonary exacerbation is reported as an Adverse Event or serious AE [SAE].

A "severe" pulmonary exacerbation is defined a pulmonary exacerbation requiring intravenous antibiotics and/or hospitalisation.

As used herein the term "inhalation" refers to the administration of a substance in the form of a nebulized liquid, gas, aerosol, or fine powder via the respiratory tract, usually by oral or nasal inhalation, for local and/or systemic effect.

As used herein the term suitable "inhalation devices" refer to devices such as: Respironics I-Neb® AAD with 0.3 mL or 0.5 mL medication chamber, Pari eFlow® rapid and Pari LC Sprint with Pari Boy® SX compressor.

These devices are characterized by the features summarized in FIG. 1 and FIG. 2.

DETAILED DESCRIPTION

According to a main aspect, the invention refers to colistimethate sodium (CMS), administered by inhalation at a dose of at least 20 mg Colistin Base Activity (CBA) per day for use in reducing the frequency of pulmonary exacerbations in patients suffering from Non-Cystic Fibrosis Bronchiectasis (NCFB) and *P. aeruginosa* infections. Said administration is preferably a "long term" administration, wherein by "long-term" is intended an administration of CBA for at least 12 months.

The use of CMS for reducing the frequency of exacerbation in NCFB has not been demonstrated until the present Clinical Phase III study (Promis I). In fact, the Phase II study failed to achieve its primary endpoint, which was set as the increase of days from the beginning of CMS treatment and the first exacerbation (Haworth, C. et al. Am. J. Respir. Crit. Care Med., 2014, 189(8), 975-982) disclosed the use of nebulized colistimethate in NCFB (PPCTP/001).

Non-cystic fibrosis bronchiectasis (NCFB) is a severe chronic illness characterized by irreversible dilation of airways and thickening of bronchial walls, chronic inflammation, repeated infections, and progressive obstruction of the airways. In contrast to cystic fibrosis bronchiectasis (CFB), which is a well-defined genetic disorder, NCFB is a heterogeneous disease caused by many different medical conditions.

Of note, medical treatments that demonstrate a clinical benefit in CFB do not necessarily show the same benefits in NCFB (Barker et al., "Aztreonam for inhalation solution in patients with non-cystic fibrosis bronchiectasis (AIR-BX1 and AIR-BX2): two randomised double blind, placebo-controlled phase 3 trials.". Lancet Respir Med, 2014, 2: 738-749) hence, direct correlation between the treatment of CFB and NCFB is not appropriate.

CMS is approved in adult and pediatric CFB patients for the management of chronic pulmonary infections due to *Pseudomonas aeruginosa*.

In view of the former clinical study on NCFB summarized above, however, it was not expected that colistin would reduce the frequency of exacerbations in NCFB patients.

Non-cystic fibrosis bronchiectasis (NCFB) is an important health issue that is increasingly common and related to a considerably high mortality. It has higher incidence in older patients and females and its incidence is increasing during the last decades due to better diagnosis means.

The main causes of NCFB are several and include infections, bronchial obstruction, allergic bronchopulmonary aspergillosis, immunodeficiency states, connective tissue disorders, idiopathic inflammatory disorders, and autoimmune diseases. The most common cause in the literature is post-infectious due to an exaggerated and uncontrolled inflammation that progressively leads to obstruction of the small airways, bronchial wall damage and destruction, and hence to bronchiectasis, although no unique underlying cause has ever been identified.

As a matter of fact, repeated respiratory infections (bacterial, viral, fungal) in susceptible individuals may lead to chronic airway inflammation, progressive obstruction of the small airways and bronchial wall destruction, which typifies non-cystic fibrosis bronchiectasis (NCFB). Once established, the airways of patients with NCFB commonly become chronically infected with bacteria often leading to recurrent exacerbations. This explanation has led to the established "vicious circle" hypothesis proposed by Cole (Cole P J, "Inflammation: a two-edged sword—the model of bronchiectasis.", European Journal of Respiratory diseases. Supplement, 1986, 147: 6-15 1986). This hypothesis consists of the following circle of events: impaired lung defences permit bacterial infection of the airway mucosa, which stimulates a neutrophilic inflammatory response that becomes chronic when it fails to eradicate the bacteria; the host inflammatory response causes tissue damage, e.g. via proteinase enzymes and reactive oxygen species which overwhelm the body's ability to neutralize them; tissue damage further impairs the lung defences, allowing bacteria to persist; and so the circle continues and disease may progress.

Other co-morbidities are more frequent in NCFB patients as compared to CFB ones. In fact, COPD (41.4%), asthma (32.8%) and gastroesophageal reflux (18.3%) are the most frequent predisposing conditions to NCFB.

Inhaled antibiotics are effective for CFB patients with *P. aeruginosa* infection, but their efficacy in NCFB has not been demonstrated. In fact, a number of pathogens are involved in the colonization of patients with bronchiectasis. The main Gram negative pathogens are: *Haemophilus influenza, Moraxella catarrhalis*, and *Pseudomonas aeruginosa*. The latter is associated with increased morbidity and mortality. Furthermore, in NCFB patients, *P. aeruginosa* strains may develop antibiotic resistance more frequently than in CFB patients.

An effective treatment according to the present invention comprises delivering a CMS amount of from at least 20 mg CBA to 60 CBA (2 MIU to 6 MIU) a day by inhalation. More preferably, CMS is administered at a dose corresponding to 10-30 mg CBA, twice a day. Even more preferably, the CMS amount is provided by inhalation at a dose of at least 10 mg CBA, corresponding to about 0.3 mL of a CMS solution comprising 30-35 mg CBA/mL, twice a day.

Preferably, NCFB patients suitable for the treatment according to the present invention have not received an antibiotic treatment with oral macrolydes and/or colistin within 30 days before the beginning of the treatment with CSM.

Inhalation by the respiratory tract, preferably inhalation by the oral route is achieved through suitable inhalation devices, such as the I-neb AAD device, which is activated by a disc provided with the I-neb and is used after appropriate training (including written instructions) which instruct also on the CMS preparation for I-neb. When a subject self-administer the Investigational medicinal product, specifically CMS, via the I-neb device, the time of day, length of nebulisation and amount of drug administered are stored in the device, thus providing a complete and faithful record of the treatment.

Other suitable devices for CMS nebulization and/or inhalation are represented, for example, in FIGS. 1 and 2.

The preferred length of CMS treatment according to the present invention is at least 12 months.

As said above, CMS dosage may be expressed differently. A conversion table (Table 1) has been provided by the European Medicines Agency to define International Units and amounts of colistimethate and colistin activity. According to this table, 1 MIU corresponds to about 80 mg colistimethate sodium (mass) and about 34 mg colistin-base activity (CBA). In the present invention we will refer to colistin-base activity (CBA).

A further embodiment according to the present invention relates to a sterile saline composition comprising colistimethate sodium (CMS), suitable for administration of an amount of CMS corresponding to at least 20 mg CBA/day by inhalation, nebulization or aerosol spray, for use in reducing the frequency of pulmonary exacerbations in patients suffering from Non-Cystic Fibrosis Bronchiectasis (NCFB) and *P. aeruginosa* infections.

Preferably the composition for inhalation is prepared at the moment of use from a suitable dose of CMS in powder. Suitable compositions comprise CMS in an amount of from at least 30-35 mg CBA/mL to 60-70 mg CBA/mL and are administered twice a day. According to a preferred embodiment, CMS is prepared in a concentration of at least 30-35 mg CBA, in 1 mL solution suitable for inhalation and about one third (0.3 mL) is delivered by inhalation, though a suitable inhalation device, delivering about 10 mg CBA each inhalation.

The sterile saline aqueous solution typically used for dispersing the colistimethate sodium in powder, preferably comprises sodium chloride (NaCl) in concentration of from 0.4% to 0.9% w/v in sterile water for injection (WFI) or a suitable physiological sterile buffered solution. The preferred final NaCl concentration in the solution for inhalation comprising CMS for use in the treatment according to the present invention, is comprised from 0.4% to 0.5% w/V, even more preferably is 0.45% w/V.

As said above, CMS compositions are preferably prepared extemporaneously, i.e. at the moment of use, or prepared and used within 24 hours, if stored at 2 to 8° C.

The present invention also refers to a kit for the reduction of the frequency of pulmonary exacerbations in patients suffering from Non-Cystic Fibrosis Bronchiectasis (NCFB) and *P. aeruginosa* infections comprising a vial with CMS in powder at a dose corresponding to at least 30-35 mg CBA Colistimethate sodium (CMS), an aqueous sterile solution and a leaflet with instruction for the treatment of NCFB by inhalation and stating that the powder has to be resuspended in about 1 mL saline and transferred to the nebulizer chamber, delivering about 0.3 mL prepared CMS composition for a long-term treatment, wherein long-term means at least 12 months.

The kit may further comprise a suitable nebulizer system, as described above.

The kit according to the present invention comprises an aqueous sterile saline solution wherein sodium chloride is in concentration of from 0.4% to 0.9% w/v, more preferably sodium chloride is in a concentration comprised from 0.4% to 0.5% w/V and even more preferably sodium chloride is present at a concentration of about 0.45% w/V.

The leaflet with instruction would recommend the use of CMS by inhalation in an amount of from at least 20 mg CBA per day, preferably an amount of CMS comprised from 20 to 60 mg CBA a day, or even more preferably at least 10 mg CBA, twice a day for at least 12 months, for reducing the frequency of pulmonary exacerbations in patients suffering from Non-Cystic Fibrosis Bronchiectasis (NCFB) and *P. aeruginosa* infections.

The reduction of the frequency of pulmonary exacerbations in patients suffering from Non-Cystic Fibrosis Bronchiectasis (NCFB) and *P. aeruginosa* infections is accompanied by an increase of the time from the beginning of treatment to the first pulmonary exacerbation of at least 180 days, more preferably 185 days, even more preferably 190, 200, 205, 206, 207 or 208 days, comprising all the intermediate values.

As said above, by pulmonary exacerbation the Applicant refers to the presence concurrently of at least 3 of the following 8 symptoms/signs for at least 24 hours:
increased cough;
increased sputum volume and/or consistency;
increased sputum purulence;
new or increased haemoptysis;
increased wheezing;
increased dyspnoea;
increased fatigue/malaise;
episodes of fever (temperature≥38° C.), and it is clinically determined that the subject requires and is prescribed systemic antibiotic therapy.

A new pulmonary exacerbation is only considered to occur if there are at least 14 days between the end of the course of systemic antibiotics and the onset of new qualifying symptoms. (Note: A pulmonary exacerbation is reported as an Adverse Event or serious AE (SAE).

"Severe" pulmonary exacerbations, are herein defined as those requiring intravenous antibiotics and/or hospitalisation;

After the study, the results on *Pseudomonas aeruginosa* density confirms that *P. aeruginosa* density falls rapidly and remains suppressed in the patients on colistimethate sodium, with no data suggestive of development of colistimethate resistance for active vs placebo groups.

According to a further embodiment, the present invention relates to a therapeutic method of reducing the frequency of pulmonary exacerbations in patients suffering from Non-Cystic Fibrosis Bronchiectasis (NCFB) and *P. aeruginosa* infections, said method comprising:

administering by inhalation to said patients colistimethate sodium (CMS) at a dose corresponding to at least 20 mg CBA/day of to reduce said frequency of said pulmonary exacerbations in said patients.

Preferably, the therapeutic method is based on the administration of a CMS dose comprised from 20 to 60 mg CBA a day.

Even more preferably the method according to the invention provides a dose of CMS corresponding to an amount of from about 10 mg CBA to about 30 mg CBA, twice a day.

In a more preferred embodiment, the dose of CMS given to a patient by inhalation is 10 mg CBA twice a day.

The method of reducing the frequency of pulmonary exacerbations in patients suffering from Non-Cystic Fibrosis Bronchiectasis (NCFB) and *P. aeruginosa* infections, comprises administering by inhalation, nebulization or aerosol spray to said patients a composition comprising at least 1 MIU/mL a day, of colistimethate sodium (CMS) (corresponding to about 33-34 mg CBA/mL and 80 mg/mL colistimethate sodium; delivering to said patients an amount of about 0.3 mL of said composition, and reducing said frequency of said pulmonary exacerbations in said patients. Preferably, said CMS is in a physiological or saline solution, wherein said saline solution is a sterile aqueous solution comprising from 0.4% to 0.9% w/v of sodium chloride. Even more preferably, said sterile saline solution comprises from 0.4% to 0.5% w/V NaCl, even more preferably 0.45% w/v of sodium chloride.

Even more preferably, said CMS is in the form of a powder to be dissolved before use in a sterile aqueous solution suitable for inhalation, wherein said powder corresponds to an amount of CMS comprised of from about 30-35 mg CBA to about 60-70 mg CBA, preferably resuspended in 1 mL sterile aqueous solution. Even more preferably the amount of CMS corresponds to at least 30-35 mg CBA, preferably 33-34 mg CBA, dissolved in 1 mL sterile aqueous solution suitable for inhalation, of which about 0.3 mL are delivered by inhalation, nebulization or aerosol spray, corresponding to about 10 mg CBA delivered during each inhalation, preferably twice a day.

Preferably the sterile aqueous solution is a saline solution, comprising from 0.4 to 0.9% w/v of sodium chloride, possibly diluted with Water for Injections.

Preferably, NCFB patients undergoing the treatment according to the present invention have not received an antibiotic treatment with oral macrolydes and/or colistin within 30 days before the beginning of the treatment with CSM.

Preferably, administration of CMS in the above mentioned preferred amounts, is long-term and continued for at least 12 months.

According to a preferred embodiment, the method of the invention comprises the preparation of a compositon for inhalation comprising CMS in an amount of from about 30-35 mg CBA, preferably about 33-34 mg CBA (corresponding to about 1 MIU CMS), preferably dissolved in 1 mL sterile aqueous saline solution and delivering by inhalation, nebulization or aerosol spray, about 10 mg CBA in 0.3 mL by I-neb, twice a day.

According to the data better detailed in the Experimental Part, the treatment according to the invention reduces the annual rate of exacerbations which is lower in patients receiving CMS I-neb vs placebo (0.58 per patient per year vs 0.95, rate ratio (RR) 0.61 95% CI 0.46-0.82, p=0.00101).

This result is highly statistically relevant.

Furthermore, the treatment induces a prolonged time to first exacerbation in the CMS I-neb group (HR: Hazard Ratio, 0.59, 95% CI 0.43-0.81, p=0.00074). Severe exacerbations (i.e. those requiring intravenous antibiotics and/or hospitalization) are also reduced (RR: Relative Risk, 0.41 95% CI 0.23-0.74, p=0.003). The percentage of patients with adverse events is similar between groups. Bronchospasm and antibiotic resistance were infrequently observed (2.8% and 1% respectively).

In particular, broncospasm was experienced clinically only in 0.6% of the patients on CMS treatment and the development of *P. aeruginosa* resistance to colistin sulphate was as low as 1%.

Therefore, CMS by I-neb significantly reduces the annual rate of exacerbations and severe exacerbations in patients with Non Cystic Fibrosis bronchiectasis and *P. aeruginosa* infection and it is safe and well tolerated.

EXPERIMENTAL PART

The clinical study PROMIS I is available at clinicaltrial.gov.

Abbreviations

AAD: Adaptive aerosol delivery

ADR: Adverse drug reaction

AE: Adverse event

CBA: Colistin Base Activity according to the table provided hereinafter (EMA indications)

CF: Cystic fibrosis

CFU: Colony forming units

CI: Confidence interval

COPD: Chronic obstructive pulmonary disease

HRCT: High-resolution Computerised Tomography

IMP: Investigational medicinal product (CMS)

IU: International Unit

MIU: Million International Unit

NCFB: Non-Cystic fibrosis bronchiectasis

SAE: Serious adverse event

Population

377 Patients were randomized (177 to CMS by I-neb) and 200 to placebo

Inclusion Criteria

Subjects were considered eligible if they:
1. are able and willing to give informed consent following a detailed explanation of participation in the protocol and signed consent obtained;
2. are aged 18 years or older of either gender;
3. are diagnosed with NCFB by computerised tomography (CT) or high resolution CT (HRCT) as recorded in the subject's notes and this is their predominant condition being treated;
4. had at least 2 NCFB pulmonary exacerbations requiring oral or inhaled antibiotics or 1 NCFB pulmonary exacerbation requiring intravenous antibiotics in the 12 months preceding the Screening Visit (Visit 1) and had no NCFB pulmonary exacerbation with or without treatment during the period between Visit 1 and Visit 2;
5. have a documented history of *P. aeruginosa* infection;
6. are clinically stable and have not required a change in pulmonary treatment for at least 30 days before the Screening Visit (Visit 1);
7. have pre-bronchodilator FEV1≥25% of predicted;
8. had a positive sputum culture for *P. aeruginosa* from an adequate sample taken at the Screening Visit (Visit 1) or during the screening period.

Exclusion Criteria

Subjects were considered not eligible if they have/are:
1. known bronchiectasis as a consequence of cystic fibrosis (CF);
2. known history of hypogammaglobulinaemia requiring treatment with immunoglobulin, unless fully replaced and considered immuno-competent by the Investigator;
3. myasthenia gravis or porphyria;
4. severe cardiovascular disease such as severe uncontrolled hypertension, ischaemic heart disease or cardiac arrhythmia and any other conditions that would confound the evaluation of safety, in the opinion of the Investigator;
5. had major surgery in the 3 months prior to the Screening Visit (Visit 1) or planned inpatient major surgery during the study period;
6. receiving treatment for allergic bronchopulmonary aspergillosis (ABPA);
7. had massive haemoptysis (greater than or equal to 300 mL or requiring blood transfusion) in the preceding 4 weeks before the Screening Visit (Visit 1) or between Visit 1 and Visit 2;
8. respiratory failure that would compromise patient safety or confound the evaluation of safety or efficacy of the study in the opinion of the Investigator;
9. current active malignancy, except for basal cell carcinoma or squamous cell carcinoma of the skin without metastases;
10. taking immunosuppressive medications (such as azathioprine, cyclosporine, tacrolimus, sirolimus, mycophenolate, rituximab), and/or anti-cytokine medications (such as anti-IL-6 and anti-tumour alpha necrosis factor products) in the preceding year before the Screening Visit (Visit 1);
11. known history of human immunodeficiency virus (HIV);
12. current treatment for non-tuberculous mycobacterial (NTM) lung disease or tuberculosis;
13. known or suspected to be allergic or unable to tolerate colistimethate sodium (intravenous or inhaled) or other polymixins, including previous evidence of bronchial hyper-reactivity following inhaled colistimethate sodium;
14. treatment with long term (≥30 days) prednisone at a dose greater than 15 mg a day (or equivalent dose of any other corticosteroid) within 6 months of the Screening Visit 1 (Visit 1);
15. new maintenance treatment with any oral macrolides (e.g. azithromycin/erythromycin/clarithromycin) started within 30 days of the Screening Visit (Visit 1) or started between Visit 1 and Visit 2;
16. use of any intravenous or intramuscular or oral or inhaled anti-pseudomonal antibiotic (except chronic oral macrolide treatment with a stable dose) within 30 days prior to the Screening Visit (Visit 1) and between Visit 1 and Visit 2;
17. pregnant or breast feeding or plan to become pregnant over the next year or of child-bearing potential and unwilling to use a reliable method of contraception for at least one month before randomisation and throughout their involvement in the trial;
18. significant abnormality in clinical evaluations and/or laboratory tests (physical examination, vital signs, haematology, clinical chemistry, clinically relevant impaired renal function, defined as serum creatinine levels≥2.0×upper limit of normal, ECG) endangering the safe participation of the patient in the study at the Screening Visit (Visit 1) and during the study;
19. participated in another investigational, interventional trial within 30 days prior to the Screening Visit (Visit 1).

Efficacy Data

Primary Endpoint

In order to investigate whether the use of inhaled colistimethate sodium reduces the frequency of pulmonary exacerbations compared to placebo in subjects with NCFB chronically infected with *P. aeruginosa*, the following hypothesis will be tested:

Null hypothesis A: there is no difference between inhaled colistimethate sodium and placebo as regards the effect on the pulmonary exacerbation rate against Alternative hypothesis A: inhaled colistimethate sodium reduces the pulmonary exacerbation rate.

The null hypothesis must be rejected for the efficacy of inhaled colistimethate sodium to be considered demonstrated.

A supportive analysis will be conducted using an alternative definition of NCFB pulmonary exacerbation. The re-classification of exacerbations will be conducted in a blinded fashion (before database lock). The alternative definition of pulmonary exacerbations used will be deterioration in three or more of the following key symptoms for at least 48 hours:

Cough

Sputum volume and/or consistency

Sputum purulence

Breathlessness and/or exercise tolerance (dyspnoea)

Fatigue and/or malaise

Haemoptysis

And:
a physician determines a change in bronchiectasis treatment is required when other potential causes of clinical deterioration have been discounted.

Mean Annual Pulmonary Exacerbation Rate

The number of NCFB pulmonary exacerbations during the treatment period will be analysed using a Poisson regression model allowing for over-dispersion including treatment, pooled sites and use of stable concomitant therapy with oral macrolides as fixed effects and log-time on trial as an offset.

The number and the percentage of subjects with NCFB pulmonary exacerbations, the number of pulmonary exacerbations and the total follow-up time in years will be summarised by treatment group. The adjusted yearly mean exacerbation rates in each treatment group and the adjusted rate ratio with their 95% CIs will be estimated by the model.

For the analysis, 2 pulmonary exacerbations will be considered as a single episode in cases where the second exacerbation starts less than 14 days after the end of the antibiotic therapy (oral or intravenous) for the first pulmonary exacerbation.

If the null hypothesis will be rejected, additional investigation of proportionality of the hazard will be implemented in a secondary analysis. Additional details on the analysis will be provided in the SAP.

A corresponding two-sided p-value of <0.05 will be considered statistically significant.

Secondary Endpoints

Summary statistics and analyses of the secondary efficacy/pharmaco-economic endpoints will be conducted for the mITT (main analysis) and the PP, as follows.

Time to First Exacerbation

The time to the first NCFB pulmonary exacerbation and the time to the first severe NCFB pulmonary exacerbation will be calculated as the time in days from the date of the first dose of IMP to the date at which the first pulmonary exacerbation occurs (i.e. date at which the first pulmonary exacerbation occurs—date of the first dose+1). A log-rank sum test will be used to compare the treatment groups. Subjects completing the trial without NCFB pulmonary exacerbations or who are discontinued prematurely without exacerbations, will be considered as censored at the time of their last follow-up.

Annualised Number of Pulmonary Exacerbation-Free Days

The annualised number of exacerbation-free days will also be presented by treatment group. An appropriate non-parametric test will be used that makes allowing for the effect of prognostic covariates possible.

Severe NCFB Pulmonary Exacerbations (Including Episodes of Pneumonia)

The number and the percentage of subjects with pneumonia and severe pulmonary exacerbations, defined as those requiring intravenous antibiotics and/or hospitalisation (admission to the hospital for longer than 24 hours), the number of pneumonias/severe pulmonary exacerbations and the annual mean pneumonia/severe pulmonary exacerbation rate will also be presented by treatment group.

Quality of Life

The SGRQ total score and domain scores (Symptoms, Activity and Impact scores) will be summarised at each visit by treatment group using descriptive statistics. Changes from baseline (Visit 2) will also be summarised for each post-baseline visit by treatment group. Scores will be computed according to the SGRQ manual [20].

Multiple entries and missing data will be dealt with as described in the same manual.

SGRQ total score will be analysed using a linear mixed model for repeated measures including treatment, visit, treatment-by-visit interaction, use of stable concomitant therapy with oral macrolides and pooled sites as fixed effects and baseline value as covariate. An unstructured covariance matrix will be assumed and the Kenward-Roger adjustment will be used for the degrees of freedom. The least square means in each treatment group, the least square mean differences between treatments, their 95% CIs and associated p-values at each visit will be estimated by the model.

The total score of the QOL-B questionnaire will be summarised and analysed similarly to the SGRQ total score. Algorithm of scoring and methods for handling with multiple imputations and missing data will be performed according to the questionnaire instructions [21, 22].

Pseudomonas aeruginosa Density

The *P. aeruginosa* density as determined by the mean change in log 10 CFU/g sputum from baseline (Visit 2) to Day 28 (Visit 3), as well as to Visits 5 and 7, will be compared between the treatment groups by an analysis of covariance model including treatment, pooled site and use of stable concomitant therapy with oral macrolides as fixed effects and baseline value as covariate. Least square means in each treatment group, least square mean difference between treatments, their 95% CIs and associated p-values will be estimated.

Sensitivity analyses may be conducted to assess the robustness of conclusions.

Summary statistics of the *P. aeruginosa* density (log 10 CFU/g sputum) and change from baseline (Visit 2) will be provided by treatment group for each trial visit.

Treatment

CMS powder 1 MIU (Xellia Pharm. Aps, Copenhagen, DK), approximately equivalent to 80 mg colistimethate sodium/33 mg Colistin Base Activity (CBA) according to table 1 was admistered by I-neb twice a day. -I-neb is a pulmonary administration device working by an ultrasonic (vibrating mesh) nebulizer system designed to aerosolize liquid medication approved for use with the I-neb AAD System. It is described e.g. in U.S. Pat. No. 6,367,470.

I-Neb (Nebulization Device)

The subjects will administer the IMP via the I-neb AAD device twice daily, activated by a disc provided with the I-neb. Subjects will receive appropriate training on the use of the I-neb device (including written instructions) and on preparation of the IMP to be used in the I-neb. Subjects will perform the first administration of IMP under supervision of the site personnel during Visit 2 and they will be informed that the device will log their IMP usage. When subjects self-administer the IMP via the I-neb device, the time of day, length of nebulisation and amount of IMP administered are stored in the device.

During the trial, adherence will be assessed on-site by the Investigator on an ongoing basis by downloading the data from the I-neb into a data analyser installed in laptops provided by the Sponsor. In addition, drug accountability, assessing the amount of IMP used and not used by a subject (see Section 11.4) will be performed. The data remains on the I-neb so it can be fully analysed at the end of the study.

After the end of treatment, i.e. Visit 7, the device use data from the I-neb will be downloaded to the laptop using instructions provided to the site personnel. The data can then be sent electronically to the CRO or Philips as per instructions. Alternatively, the device can be stored and returned to Almac with returned IMP. Almac will then send the device on to Philips (the I-neb manufacturer) who will download the data and send it on to the CRO. As the I-neb system records all information on the doses of IMP taken, these data will be used to determine overall adherence.

Pseudomonas aeruginosa Analysis

Results of the quantitative analysis for *P. aeruginosa* density will be presented as colony forming units (CFU) count per gram sputum.

Besides *P. aeruginosa* density analysis (see Section 9.1.5), the susceptibility of *P. aeruginosa* to colistin sulphate will be evaluated from the sputum samples collected at each visit. The susceptibility testing will be done using a minimal inhibitory concentration (MIC) method. Testing of susceptibility with other antibacterial panels will also be conducted for samples collected during pulmonary exacerbations.

If resistance to colistin sulphate is detected and/or any isolate shows a significant rise in MIC (i.e. showing greater than a four-fold change in colistimethate sodium MIC) genotyping studies on P. aeruginosa isolates may be conducted to determine if the change in MIC is due to microbiological recurrence or re-infection.

The results have shown that P. aeruginosa density fell rapidly and remained suppressed in those on colistimethate sodium, with no data suggestive of development of colistimethate resistance for active vs placebo groups.

| Mean change from baseline in P. aeruginosa density [$\log_{10}$(CFU/mL)] (mITT) | Colistimethate sodium (n = 176) | Placebo (n = 197) |
| --- | --- | --- |
| Visit 3 (28 days) | −1.59 | −0.03 |
| Visit 5 (6 months) | −1.39 | 0.02 |
| Visit 6 (9 months) | −1.56 | 0.01 |
| Visit 7 (12 months/EOT)* | −0.86 | −0.08 |

*Visit 7/EOT counts were slightly higher than Visit 6 as this included those who discontinued early.
mITT: modified Intention to Treat Biometrics
Primary Efficacy Variable:
The primary variable for this trial is the mean annual NCFB pulmonary exacerbation rate (frequency of pulmonary exacerbations) over 12 months.
Secondary Efficacy Variables:
The time (in days) from the first dose of IMP until the first pulmonary exacerbation;
annualised number of pulmonary exacerbation-free days;
number of severe pulmonary exacerbations, defined as those requiring intravenous antibiotics and/or hospitalisation;
the time (in days) from the first dose of IMP until the first severe pulmonary exacerbation;
QoL as measured by the total scores of the SGRQ and QOL-B questionnaires as well as changes in SGRQ and QOL-B from baseline to each post-baseline visit;
number of days of work absence due to pulmonary exacerbations;
P. aeruginosa density as determined by the mean change in log 10 CFU/g sputum from baseline (Visit 2) to Day 28 of treatment (Visit 3) as well as to Visits 5 and 7.
Safety Variables
incidence of TEAEs;
absolute changes in percent-predicted FEV1 from baseline (Visit 2) to end of treatment (Visit 7);
number of subjects experiencing bronchospasm clinically or spirometrically determined following IMP administration at the start and end of treatment;
P. aeruginosa resistance to colistin sulphate as determined by in-vitro susceptibility testing on sputum from Screening/Randomisation (Visit 1/Visit 2) to Visits 3, 5 and end of treatment (Visit 7) as well as on sputum from Exacerbation Visits and clinic visits due to pneumonia;
emergence of other bacterial colonies and any developing resistance in sputum from Screening (Visit 1) to End of Treatment (Visit 7);
haematology, clinical chemistry and renal function tests;
physical examination and vital signs data;
12-lead electrocardiogram Results The annual rate of exacerbations was lower in patients receiving CMS I-neb vs placebo (0.58 per patient per year vs 0.95, rate ratio (RR=Relative Risk) 0.61 95% CI 0.46-0.82, p=0.00101).
This result is highly statistically relevant.
There was a prolonged time to first exacerbation in the CMS I-neb group (HR 0.59, 95% CI 0.43-0.81, p=0.00074; HR=Hazard Ratio). Severe exacerbations (i.e. those requiring intravenous antibiotics and/or hospitalization) were also reduced (RR 0.41 95% CI 0.23-0.74, p=0.003). The percentage of patients with adverse events was similar between groups. Bronchospasm and antibiotic resistance were infrequently observed (2.8% and 1% respectively).
In particular, broncospasm was experienced clinically only in 0.6% of the patients on CMS treatment and the development of P. aeruginosa resistance to colistin sulphate was as low as 1%.
Therefore, CMS by I-neb significantly reduced the annual rate of exacerbations and severe exacerbations in patients with bronchiectasis and P. aeruginosa. The treatment was safe and well tolerated.

The invention claimed is:
1. A method of reducing the frequency of pulmonary exacerbations in patients suffering from Non-Cystic Fibrosis Bronchiectasis (NCFB) and P. aeruginosa infections, said method comprising:
administering by inhalation to said patients a dose of from 20 mg Colistin Based Activity (CBA) as colistimethate sodium (CMS) a day to 60 mg CBA as CMS/day; and
reducing said frequency of said pulmonary exacerbations in said patients, wherein said patients had at least two NCFB pulmonary exacerbations requiring oral or inhaled antibiotics or one NCFB pulmonary exacerbation requiring intravenous antibiotics in the 12 months preceding the inhalatory CMS administration and wherein said patients did not have any NCFB pulmonary exacerbation for at least 30 days before the beginning of the inhalatory CMS administration.
2. The method according to claim 1, wherein said dose is of from 10 mg CBA to 30 mg CBA twice a day.
3. The method according to claim 2, wherein said dose is 10 mg CBA twice a day.
4. The method according to claim 1, wherein said CMS is administered for at least 12 months.
5. The method according to claim 1 comprising:
administering by inhalation to said patients a dose of at least 10 mg CBA twice a day for at least 12 months; and
reducing said frequency of said pulmonary exacerbations in said patients.
6. The method according to claim 1, wherein said patients are diagnosed with NCFB by computerized tomography (CT) or high resolution CT (HRCT).

* * * * *